United States Patent [19]

Hartman et al.

[11] Patent Number: 5,270,195

[45] Date of Patent: Dec. 14, 1993

[54] PLASMIDS FOR EXPRESSION AND METHOD OF PRODUCING A HUMAN MANGANESE SUPEROXIDE DIMUTASE ANALOG

[75] Inventors: Jacob R. Hartman, Holon; Yaffa Beck, Gadera, both of Israel

[73] Assignee: Bio-Technology General Corp., New York, N.Y.

[21] Appl. No.: 912,213

[22] Filed: Jul. 10, 1992

Related U.S. Application Data

[63] Continuation of Ser. No. 453,057, Dec. 13, 1989, which is a continuation of Ser. No. 32,734, Sep. 27, 1987, abandoned, which is a continuation-in-part of Ser. No. 907,051, Sep. 12, 1986, abandoned, which is a continuation-in-part of Ser. No. 801,090, Nov. 22, 1985, abandoned.

[30] Foreign Application Priority Data

Oct. 29, 1986 [IE] Ireland .............................. 2851/86

[51] Int. Cl.$^5$ .......................... C12N 9/02; C12N 1/21; C12N 15/53
[52] U.S. Cl. ................................ 435/189; 435/252.33; 435/320.1
[58] Field of Search ................ 435/189, 320.1, 252.33

[56] References Cited

U.S. PATENT DOCUMENTS

| | | | |
|---|---|---|---|
| 3,920,521 | 11/1975 | Michelson et al. | 195/55 |
| 4,129,644 | 12/1978 | Kalopissis et al. | 424/59 |
| 4,425,437 | 1/1984 | Riggs | 435/47 |
| 4,695,456 | 9/1987 | Wilder | 424/94.5 |
| 4,742,004 | 5/1988 | Hartman et al. | 435/70 |
| 4,751,180 | 6/1988 | Cousens et al. | 435/68 |

FOREIGN PATENT DOCUMENTS 0138111 of 1985 European Pat. Off.

OTHER PUBLICATIONS

Jacob M. McCord and Irwin Fridovich, Superoxide Dismutase, *J. Biol. Chem.* 244(22): 6049–6055 (1969).
Judy Lieman-Hurwitz, et al., Human cytoplasmic superoxide dismustase cDNA clone: A probe for studying the molecular biology of Down syndrome, Proc. Natl. Acad. Sci. USA 79: 2808–2811 May 1982.
Stryer, L., Biochemistry, W. H. Freeman and Co., San Francisco p. 18 (1975).
Coombs, J., Dictionary of Biotechnology, Elsevier, New York p. 248 (1986).
Steinman, H. M., Superoxide Dismutase (Oberly, ed.), CRC Press, Florida pp. 11–68.
Barra, D. et al., FEBS Letters 120: 53–56 (1980).
Touati, D., J. of Bacteriology 155(3): 1078–1087 (1983).
Takeda, Y. et al., Nucleic Acids Res. 14(11): 4577–4589 (1986).
Beck, Y., et al., Nucleic Acids Res. 15(21): 9076 (1987).
Barra, D., et al., Proceedings of the Third Int'l. Conf. on Superoxide and SOD, vol. 1, pp. 336–339, Elsevier Science Publishing Co. (1983).
Barra, D., et al., Chemical Abstracts 100(19771g) (1984).
Suggs et al. (1981), Proc. Natl. Acad. Sci., vol. 78, No. 11, pp. 6613–6617.
Barra et al., *J. Biol. Chem.* 259:12595–601, 1984.

*Primary Examiner*—Charles L. Patterson, Jr.
*Attorney, Agent, or Firm*—John P. White

[57] ABSTRACT

An expression plasmid has been constructed which includes DNA encoding human manganese superoxide dismutase. Such plasmids may be introduced into host cells and the resulting cells cultured or grown under suitable conditions so as to produce enzymatically active human manganese superoxide dismutase or analogs thereof which may then be recovered. A method of producing an enzymatically active analog of human manganese superoxide dismutase by supplementing the culture media with $Mn^{++}$ has been developed.

21 Claims, 14 Drawing Sheets

FIGURE 1A

```
GAATTCGGCCG GCGGCATCAG CGGCTAAGCC AGCACTAGCA GC ATG TTG AGC CGG              54
                                                  Met Leu Ser Arg
                                                   1

GCA GTG TGC GGC ACC AGC AGG CAG CTG GCT CCG GCT TTG GGG TAT CTG             102
Ala Val Cys Gly Thr Ser Arg Gln Leu Ala Pro Ala Leu Gly Tyr Leu
          5                  10                  15                  20

GGC TCC AGG CAG AAG CAC AGC CTC CCC GAC CTG CCC TAC GAC TAC GGC             150
Gly Ser Arg Gln Lys His Ser Leu Pro Asp Leu Pro Tyr Asp Tyr Gly
              25                  30                  35

GCC CTG GAA CCT CAC ATC AAC GCG CAG ATC ATG CAG CTG CAC CAC AGC             198
Ala Leu Glu Pro His Ile Asn Ala Gln Ile Met Gln Leu His His Ser
              40                  45                  50

AAG CAC CAC GCG GCC TAC GTG AAC CTG AAC GTC ACC GAG GAG AAG                 246
Lys His His Ala Ala Tyr Val Asn Leu Asn Val Thr Glu Glu Lys
              55                  60                  65

TAC CAG GAG GCG TTG GCC AAG GGA GAT GTT ACA GCC CAG ATA GCT CTT             294
Tyr Gln Glu Ala Leu Ala Lys Gly Asp Val Thr Ala Gln Ile Ala Leu
      70                  75                  80

CAG CCT GCA CTG AAG TTC AAT GGT GGT CAT ATC AAT CAT AGC ATT                 342
Gln Pro Ala Leu Lys Phe Asn Gly Gly His Ile Asn His Ser Ile
          85                  90                  95                  100
```

FIGURE 1B

```
TTC TGG ACA AAC CTC AGC CCT AAC GGT GGT GGA GAA CCC AAA GGG GAG      390
Phe Trp Thr Asn Leu Ser Pro Asn Gly Gly Gly Glu Pro Lys Gly Glu
        105                     110                     115

TTG CTG GAA GCC ATC AAA CGT GAC TTT GGT TCC TTT GAC AAG TTT AAG      438
Leu Leu Glu Ala Ile Lys Arg Asp Phe Gly Ser Phe Asp Lys Phe Lys
            120                     125                     130

AG AAG CTG ACG GCT GCA TCT GTT GGT GTC CAA GGC TCA GGT TGG GGT       486
 lu Lys Leu Thr Ala Ala Ser Val Gly Val Gln Gly Ser Gly Trp Gly
        135                     140                     145

TGG CTT GGT TTC AAT AAG CAA TTA CGG GGA CAC TTA CAA ATT GCT GCT TGT  534
Trp Leu Gly Phe Asn Lys Gln Leu Arg Gly His Leu Gln Ile Ala Ala Cys
150                     155                     160

CCA AAT CAG GAT CCA CTG CAA GGA ACA ACA GGC CTT ATT CCA CTG CTG      582
Pro Asn Gln Asp Pro Leu Gln Gly Thr Thr Gly Leu Ile Pro Leu Leu
165                     170                     175                180

GGG ATT GAT GTG TGG GAG CAC GCT TAC TAC CTT CAG TAT AAA AAT GTC      630
Gly Ile Asp Val Trp Glu His Ala Tyr Tyr Leu Gln Tyr Lys Asn Val
            185                     190                     195
```

FIGURE 1C

```
AGG CCT GAT TAT CTA AAA GCT ATT TGG AAT GTA ATC AAC TGG GAG AAT       678
Arg Pro Asp Tyr Leu Lys Ala Ile Trp Asn Val Ile Asn Trp Glu Asn
            200                 205                 210

GTA ACT GAA AGA TAC ATG GCT TGC AAA AAG TAAACCACGA TCGTTATGCT         728
Val Thr Glu Arg Tyr Met Ala Cys Lys Lys
        215                 220

GATCATACCC TAATGATCCC AGCAAGATAA TGTCCTGTCT TCTAAGATGT GCATCAAGCC     788

TGGGTACATA CTGAAACCCC GAATT                                           813
```

FIGURE 6A

```
AACCAAAAAC TCACGGGGCC AGCGCCGGCA GGGCCGCCTA GTGCAGCCAG ATCCCCGCCG      60
GCACCTCAGG GGGGGACCC  GCAGGCAGGG CTTGCGGGCC GTACCAACTG CCACGGGGGC    120
                     ─────1
AGGGGCCGCC TCCCTTCGGC CGCGCCCAC  TGCAAGTACG GCAGGACACC AGCGAGGTTG    180
                                     1
CCGAGGCCGA GGCTAGCCTG CAGCCTCCTT TCTCCCGTGC CCTGGGCGCG GGGTGTACGG    240
                                           ─────2
CAAGCGCGGG CGGGGGGAC  AGGCACGCAG GGCACCCCCG GGGTTCGGGC GCGGGGGCG     300
       ─────4                                  2           ────
GGGCGGGGC  TCGGGGGGG  AGGGGGCGGG GCCGGGGTCG CCCTTGTCGG CGCAGCTGGG    360
                                                            3
TCGCGGCCCT GCTCCCCGGCG CTTTCTTAAG GCCCGCGGGC GGGCAGGAG CGGTCACTCG    420
      ↑                                                ─────
TGGCTGTGGT GGCTTCCCGA GGGCCTTCAG CAGATGGGGG GCATGAGGGG TAAGCCAGCA    480
CTAGCAGCAT GTTGAGCCGG GCAGTGTGCC GGTGAGAAGG AAGGGGACCC GGTCACGCCCC   540
CAAGGGGAAG GGGCTCGCGG CGGGCAGGGC CGGCGACCTG GGCGACATGG CCGCACGGGC    600
CTGGCGGGAC CGCCGACCTG CAGGCGGTTC TCCCGGGAGT TCCCGGGCCG GCGGCCTGGA    660
GCCGGGGATC CGAGGGAGGG GACGCGGGGA CTCGGGGGAC GCCGGCGTGC GTTCCTCGGC    720
```

FIGURE 6B

```
AGCCCAGCCT GCGTAGACGG TCCGCGGCGC TGACTGACCG GGCTGTGCTT TCTCGTCTTC           780
AGGCACCAGC AGGCAGCTGG CTCCGGTTTT GGGGTATCTG GGCTCCAGGC AGAGCACAG            840
CCTCCCCGAC CTGCCCTACG ACTACGGGGG CCTGGAACCT CACATCAACG CGCAGATCAT           900
GCAGTGCAC CACAGCAGC ACCAGGCCGG CTAGGTGAAC AACTGAACG TCACCGAGGA              960
GAAGTACCAG GAGGCGGTGG CCAAGGGTAG GTTCCAGGCT GAGCGGG...............          1020
AAAAAAATGT GGTTTGCACT TTTAACTTTT AAGGAGATGT TACAGCCCAG ATAGCTCTTC           1080
AGCCTGCACT GAAGTTCAAT GGTGGTGGTC ATATCAATCA TAGCATTTTC TGGACAAACC           1140
TCAGCCCTAA CGGTGGTGGA GAACCCAAG GTTGGATATA TTGTGCACCC TTATCTACAA            1200
CTTCTTGCAC AGTAGGAATC GAT...........................                       1260
GTAATTTCTT GGGCCCTATG ACAAAAAATA TTTGAATAC ATGTAATATA ACATTTTACT            1320
GTAATTATTG GAAATCTGTT CATTGTGGG TGGTTTTGGG ATTTTTTTTT TAATAGGGGA            1380
GTTGCTGGAA GCCATCAAAC GTGACTTTGG TTCCTTTGAC AAGTTTAAGG AGAAGCTGAC           1440
```

FIGURE 6C

```
GGCTGCATCT GTTGGTGTCC AAGGCTCAGG TTGGGGTTGG CTTGGTTTCA ATAAGCAACG 1500
GGGACACTTA CAAATTGCTG CTTGTCCAAA TCAGGATCCA CTCCAAGGAA CAACAGGTTA 1560
CATTTAGATA GGGTTGAGTG TTGTTCCAGT TTGGAAAACG AGTCCACTAT TAAAGAACGT 1620
CGACTCCAAC GTCAAAGGGC GAAAAACCGT CTATCAGGGC GATGGCCACT ACGTGAACCA 1680
TCACCCAAAT CAAGTTTTTT GGGGTCGAGG TGCCGTGAAA GCACTAAATC GGAACCTAAA 1740
GGGAGCCCCC GATTTAGAGC TTGACGGGGA AAGCCGGGCG AACTGTGGCG AGAAAGGAAG 1800
GAAGAAAGC GAAAGGAGCG GGCGCTAGGC GTGGCAATTG CTGTAGCGTCA CTGGCG...... 1860
CCCCTTCTT TCTAACAGGC CTTATTCCAC TGCTGGGGAT TGATGTGTGG GAGCACGCTT 1920
ACTACCTTCA GTATAAAAT GTCAGGCCCTG ATTATCTAAA AGTATTGG AATGTAATCA 1980
ACTGGGAGAA TGTAACTGAA AGATACATGG CTTGCAAAA GTAACCACG ATCGTTATGC 2040
AGAGTATGTT AAGCTCTTTA TGACTGACTA TGTAGTGGTA TAGAGTACTG CAGX...... 2100
GTCCATATCT AAAACCACGT ATAAACATTA AATTGTATTT CCTGTTTTAA TTCCAGGGGA 2160
```

FIGURE 6D

```
AGTACTGTTT GGGAAAGCTA TTATTAGGTA AATGTTTTAC AAATTACTGT TTCTCAGTTT   2220
CAGTCATACC CTAATGATCC CAGCAAGATA ATGTCCTGTC TTCTAAGATC TCCATCAAGC   2280
TGGGTACAT ACTGAAACCC TATAAGGTCC CTGGATAATT TTTGTTTGAT TATTGCATTG   2340
AGAAACATT TATTTCCAA AATTGTGTGA AGTTTTTGAC TGTTAATAAA AGAATCTGTC    2400
AACCATCAAA GAGGTCTGCA TTAATGCTTG CATGTCTTTT TCATTAAAAA TCCTATAATC  2460
TTCTGTCATT TTCACTGAGT TTCCATGGGA AAGGAATAGT AAACTAATGG GTAGTTGAAA  2520
TATTACTCTT AAGACCAAGA CCTGTGTCTC CAGTCATATC TGTAATAACA TCATCTGATA  2580
CCTAAAAGC ATAGTATTAG GGATATACGA CAAAACCAAA GTGTTTTTGC TGTTGTCACA   2640
TACCACTCAA TACTTTTACA CCAGTTTGTC CAGTGGGACT CCAGCTG...  ........   2700
```

|           | EXON   | INTRON          | EXON   |
|-----------|--------|-----------------|--------|
| INTRON #1 | TGTGCG | GGTGAG...CTTCAG | GCACCA |
| INTRON #2 | CCAAGG | GTAGGT...TTTAAG | GAGATG |
| INTRON #3 | CCAAAG | GTTGGA...TAATAG | GGGAGT |
| INTRON #4 | CAACAG | GTTACA...TAACAG | GCCTTA |
| INTRON #5 | TGCTGA | GTATGT...TTTCAG | TCATAC |

```
                             A        TT
CONSENSUS             AG   GT AGT... NCAG     G
                             G        CC
```

PLASMIDS FOR EXPRESSION AND METHOD OF PRODUCING A HUMAN MANGANESE SUPEROXIDE DIMUTASE ANALOG

This application is a continuation of U.S. Ser. No. 453,057, filed Dec. 13, 1989, which is a continuation of U.S. Ser. No. 032,734, filed Mar. 27, 1987, now abandoned; which was a continuation-in-part of U.S. Ser. No. 907,051, filed Sep. 12, 1986, now abandoned; which was a continuation-in-part of U.S. Ser. No. 801,090, filed Nov. 22, 1985, now abandoned, the contents of which are hereby incorporated by reference into the subject application.

BACKGROUND OF THE INVENTION

Throughout this application, various publications are referenced by arabic numerals within parentheses. Full citations for these references may be found at the end of the specification immediately preceding the claims. The disclosures of these publications in their entireties are hereby incorporated by reference into this application in order to more fully describe the state of art as known to those skilled therein as of the date of the invention described and claimed herein.

Superoxide dismutase (SOD) and the phenomenon of oxygen free radicals ($O_2-$) was discovered in 1968 by McCord and Fridovich (1). Superoxide radicals and other highly reactive oxygen species are produced in every respiring cell as by-products of oxidative metabolism, and they have been shown to cause extensive damage to a wide variety of macromolecules and cellular components (for review see 2,3). A group of metalloproteins known as superoxide dismutases catalyze the oxidation-reduction reaction $2O_2- + 2H^+ \rightarrow H_2O_2 + O_2$ and thus provide a defense mechanism against oxygen toxicity. There are several known forms of SOD containing different metals and different proteins. Metals present in SOD include iron, manganese, copper and zinc. All of the known forms of SOD catalyze the same reaction. These enzymes are found in several evolutionary groups. Superoxide dismutases containing iron are found primarily in prokaryotic cells. Superoxide dismutases containing copper and zinc have been found in virtually all eukaryotic organisms (4). Superoxide dismutases containing manganese have been found in organisms ranging from microorganisms to man.

Since every biological macromolecule can serve as a target for the damaging action of the abundant superoxide radical, interest has evolved in the therapeutic potential of SOD. The scientific literature suggests that SOD may be useful in a wide range of clinical applications. These include prevention of oncogenesis and of tumor promotion, and reduction of the cytotoxic and cardiotoxic effects of anticancer drugs (10), protection of ischemic tissues (12) and protection of spermatozoa (13). In addition, there is interest in studying the effect of SOD on the aging process (14).

The exploration of the therapeutic potential of human SOD has been limited mainly due to its limited availability.

Superoxide dismutase is also of interest because of its anti-inflammatory properties (11). Bovine-derived superoxide dismutase (orgotein) has been recognized to possess anti-inflammatory properties and is currently marketed in parts of Europe as a human pharmaceutical. It is also sold in the United States as a veterinary product, particularly for the treatment of inflamed tendons in horses. However, supplies of orgotein are limited. Prior techniques involving recovery from bovine or other animal cells have serious limitations and the orgotein so obtained may produce allergic reactions in humans because of its non-human origin.

Copper zinc superoxide dismutase (CuZn SOD) is the most studied and best characterized of the various forms of superoxide dismutase.

Human CuZn SOD is a dimeric metallo-protein composed of identical non-covalently linked subunits, each having a molecular weight of 16,000 daltons and containing one atom of copper and one of zinc (5). Each subunit is composed of 153 amino acids whose sequence has been established (6,7).

The cDNA encoding human CuZn superoxide dismutase has been cloned (8). The complete sequence of the cloned DNA has also been determined (9). Moreover, expression vectors containing DNA encoding superoxide dismutase for the production and recovery of superoxide dismutase in bacteria have been described (24,25). The expression of a superoxide dismutase DNA and the production of SOD in yeast has also been disclosed (26).

Recently, the CuZn SOD gene locus on human chromosome 21 has been characterized (27) and recent developments relating to CuZn superoxide dismutase have been summarized (28).

Much less is known about manganese superoxide dismutase (MnSOD). The MnSOD of E. coli K-12 has recently been cloned and mapped (22). Barra et al. disclose a 196 amino acid sequence for the MnSOD polypeptide isolated from human liver cells (19). Prior art disclosures differ, however, concerning the structure of the MnSOD molecule, particularly whether it has two or four identical polypeptide subunits (19,23). It is clear, however, that the MnSOD polypeptide and the CuZn SOD polypeptide are not homologous (19). The amino acid sequence homologies of MnSODs and FeSOD from various sources have also been compared (18).

Baret et al. disclose in a rat model that the half life of human MnSOD is substantially longer than the half-life of human copper SOD; they also disclose that in the rat model, human MnSOD and rat copper SOD are not effective as anti-inflammatory agents whereas bovine copper SOD and human copper SOD are fully active (20).

McCord et al. disclose that naturally occurring human manganese superoxide dismutase protects human phagocytosing polymorphonuclear (PMN) leukocytes from superoxide free radicals better than bovine or porcine CuZn superoxide dismutase in "in vitro" tests (21).

The present invention concerns the preparation of a cDNA molecule encoding the human manganese superoxide dismutase polypeptide or an analog or mutant thereof. It is also directed to inserting this cDNA into efficient bacterial expression vectors, to producing human MnSOD polypeptide, analog, mutant and enzyme in bacteria, to recovering the bacterially produced human MnSOD polypeptide, analog, mutant or enzyme. This invention is also directed to the human MnSOD polypeptides, analogs, or mutants thereof so recovered and their uses.

This invention further provides a method for producing enzymatically active human MnSOD in bacteria, as well as a method for recovering and purifying such enzymatically active human MnSOD.

The present invention also relates to a DNA molecule encoding the human MnSOD gene. It is also directed to inserting the DNA into mammalian cells to produce MnSOD polypeptide, analog, mutant and enzyme.

The present invention also relates to using human manganese superoxide dismutase or analogs or mutants thereof to catalyze the reduction of superoxide radicals to hydrogen peroxide and molecular oxygen. In particular, the present invention concerns using bacterially produced MnSOD or analogs or mutants thereof to reduce reperfusion injury following ischemia and prolong the survival period of excised isolated organs. It also concerns the use of bacterially produced MnSOD or analogs thereof to treat inflammations.

SUMMARY OF THE INVENTION

A DNA molecule which includes cDNA encoding the human manganese superoxide dismutase polypeptide or analog or mutant thereof has been isolated from a human T-cell cDNA library. The nucleotide sequence of a double-stranded DNA molecule which encodes human manganese superoxide dismutase polypeptide or analog or mutant thereof has been discovered. The sequence of one strand encoding the polypeptide or analog thereof is shown in FIG. 1 from nucleotide 115 downstream to nucleotide 708 inclusive. Other sequences encoding the analog or mutant may be substantially similar to the strand encoding the polypeptide. The nucleotide sequence of one strand of a double stranded DNA molecule which encodes a twenty-four (24) amino acid prepeptide is also shown in FIG. 1, from nucleotides number 43 through 114, inclusive.

The double-stranded cDNA molecule or any other double-stranded DNA molecule which contains a nucleotide strand having the sequence encoding the human manganese superoxide dismutase polypeptide or analog or mutant thereof may be incorporated into a cloning vehicle such as a plasmid or virus. Either DNA molecule may be introduced into a cell, either procaryotic, e.g., bacterial, or eukaryotic, e.g., yeast or mammalian, using known methods, including but not limited to methods involving cloning vehicles containing either molecule.

Preferably the cDNA or DNA encoding the human manganese superoxide dismutase polypeptide or analog or mutant thereof is incorporated into a plasmid, e.g., pMSE-4 or pMSΔRB4, and then introduced into a suitable host cell where the DNA can be expressed and the human manganese superoxide dismutase (hMnSOD) polypeptide or analog or mutant thereof produced. Preferred host cells include *Escherichia coli*, in particular *E. coli* A4255 and *E. coli* A1645. The plasmid pMSE-4 in *E. coli* strain A4255 has been deposited with the American Type Culture Collection under ATCC Accession No. 53250. The plasmid pMS RB4 may be obtained as shown in FIG. 4 and described in the Description of the Figures.

Cells into which such DNA molecules have been introduced may be cultured or grown in accordance with methods known to those skilled in the art under suitable conditions permitting transcription of the DNA into mRNA and expression of the mRNA as protein. The resulting manganese superoxide dismutase protein may then be recovered.

Veterinary and pharmaceutical compositions containing human MnSOD or analogs or mutants thereof and suitable carriers may also be prepared. This human manganese superoxide dismutase or analogs or mutants may be used to catalyze the following reaction:

$$2O_2^- + 2H^+ \rightarrow H_2O_2 + O_2$$

and thereby reduce cell injury caused by superoxide radicals.

More particularly, these enzymes or analogs or mutants thereof may be used to reduce injury caused by reperfusion following ischemia, increase the survival time of excised isolated organs, or treat inflammations.

This invention is directed to a method of producing enzymatically active human manganese superoxide dismutase or an analog or mutant thereof in a bacterial cell. The bacterial cell contains and is capable of expressing a DNA sequence encoding the human manganese superoxide dismutase or analog or mutant thereof. The method comprises maintaining the bacterial cell under suitable conditions and in a suitable production medium. The production medium is supplemented with an amount of $Mn^{++}$ so that the concentration of $Mn^{++}$ available to the cell in the medium is greater than about 2 ppm.

In a preferred embodiment of the invention the bacterial cell is an *Escherichia coli* cell containing a plasmid which contains a DNA sequence encoding for the human manganese superoxide dismutase polypeptide e.g. pMSE-4 or pMSΔRB4 in *E. coli* strain A4255. The concentration of $Mn^{++}$ in the production medium ranges from about 50 to about 1500 ppm, with concentrations of 150 and 750 ppm being preferred.

This invention also concerns a method of recovering manganese superoxide dismutase or analog thereof from bacterial cells which contain the same. The cells are first treated to recover a protein fraction containing proteins present in the cells including human manganese superoxide dismutase or analog or mutant thereof and then the protein fraction is treated to recover human manganese superoxide dismutase or analog or mutant thereof. In a preferred embodiment of the invention, the cells are first treated to separate soluble proteins from insoluble proteins and cell wall debris and the soluble proteins are recovered. The soluble proteins are then treated to separate, e.g. precipitate, a fraction of the soluble proteins containing the hMnSOD or analog or mutant thereof and the fraction containing the hMnSOD or analog or mutant is recovered. The recovered fraction of soluble proteins is then treated to separately recover the human manganese superoxide dismutase or analog thereof.

A more preferred embodiment of the invention concerns a method of recovering human manganese superoxide dismutase or analog or mutant thereof from bacterial cells which contain human manganese superoxide dismutase or analog or mutant thereof. The method involves first isolating the bacterial cells from the production medium and suspending them in suitable solution having a pH of about 7.0 to 8.0. The cells are then disrupted and centrifuged and the resulting supernatant is heated for about 30 to 120 minutes at a temperature between 55° and 65° C., preferably for 45-75 minutes at 58°-62° C. and more preferably for 1 hour at 60° C. and then cooled to below 10° C., preferably to 4° C. Any precipitate which forms is to be removed e.g. by centrifugation, and the cooled supernatant is dialyzed against an appropriate buffer e.g. 2 mM potassium phosphate buffer having a pH of about 7.8. Preferably, the dialysis is by ultrafiltration using a filtration membrane smaller than 30K. Simultaneously with or after dialysis the cooled supernatant optionally may be concentrated to an appropriate convenient volume e.g. 0.03 of its original volume. The retentate is then eluted on an anion exchange chromatography column with an appropriate buffered solution e.g. a solution of at least 20 mM potassium phosphate buffer having a pH of about 7.8. The fractions of eluent containing superoxide dismutase are collected, pooled and dialyzed against about 40 mM potassium acetate, pH 5.5. The dialyzed pooled fractions are then eluted through a cation exchange chromatography column having a linear gradient of about 40 to about 200 mM potassium acetate and a pH of 5.5. The peak fractions containing the superoxide dismutase are collected and pooled. Optionally the pooled peak fractions may then be dialyzed against an appropriate solution e.g. water or a buffer solution of about 10 mM potassium phosphate buffer having a pH of about 7.8.

The invention also concerns purified enzymatically active human manganese superoxide dismutase or analogs thereof e.g. met-hMnSOD, or mutants produced by the methods of this invention.

The present invention also relates to a DNA molecule encoding the human MnSOD gene. The nucleotide sequence of the exon coding regions of one strand of the MnSOD gene is shown in 6. The DNA encoding the MnSOD gene may be incorporated into a cloning vehicle such as a plasmid or a virus. The DNA or the cloning vehicle may be introduced into eucaryotic cells using known methods. Preferably, the DNA encoding the human manganese superoxide dismutase gene is encoded in the plasmids pMSG11-1, pMSG4 and pMSG-1b. The eucaryotic cells which are transformed are preferably mammalian cell lines such as the human HeLa cell line or the mouse L cell line. Another aspect of this invention is the production of the human manganese superoxide dismutase polypeptide, analog, mutant or enzyme by growing the cells of this invention in suitable medium under suitable conditions.

BRIEF DESCRIPTION OF THE FIGURES

FIG. 1A-1C. The Sequence of human MnSOD cDNA

FIG. 1 shows the nucleotide sequence of one strand of a double-stranded DNA molecule encoding the human manganese superoxide dismutase as well as the 198 amino acid sequence of human MnSOD corresponding to the DNA sequence. FIG. 1 also shows the nucleotide sequence of one strand of a double stranded DNA molecule encoding a prepeptide to the mature human MnSOD consisting of twenty-four amino acids and the amino acid sequence corresponding to that DNA sequence. Also shown are parts of the 5' and 3' untranslated sequences.

Figure 2:
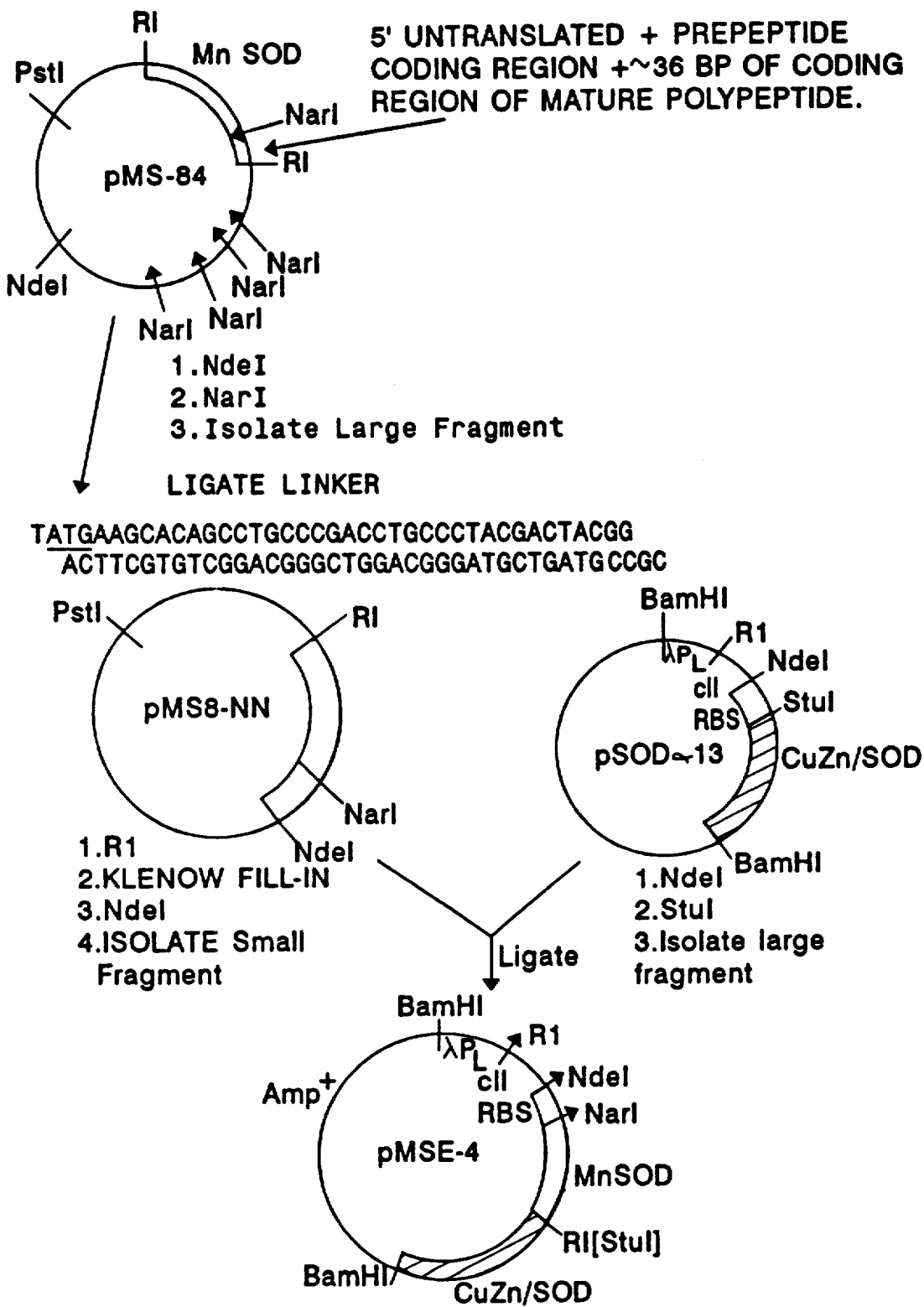
FIG. 2. Construction of pMSE-4: Human MnSOD Expression Plasmid

Plasmid pMS8-4, containing MnSOD on an EcoRI ($R_1$) insert, was digested to completion with NdeI and NarI restriction enzymes. The large fragment was isolated and ligated with a synthetic oligomer as depicted in FIG. 2. The resulting plasmid, pMS8-NN contains the coding region for the mature MnSOD, preceded by an ATG initiation codon. The above plasmid was digested with EcoRI, ends were filled in with Klenow fragment of Polymerase I and further cleaved with NdeI. The small fragment harboring the MnSOD gene was inserted into pSOD 13 which was treated with NdeI and StuI. pSOD - 13 may be obtained as described in pending co-assigned U.S. patent application Ser. No. 644,245, filed Aug. 27, 1984 which is hereby incorporated by reference. This generated plasmid pMSE-4 containing the MnSOD coding region preceded by the cII ribosomal binding site and under the control of λ $P_L$ promoter. Plasmid pMSE-4 has been deposited with the American Type Culture Collection under ATCC Accession No. 53250.

Figure 3:
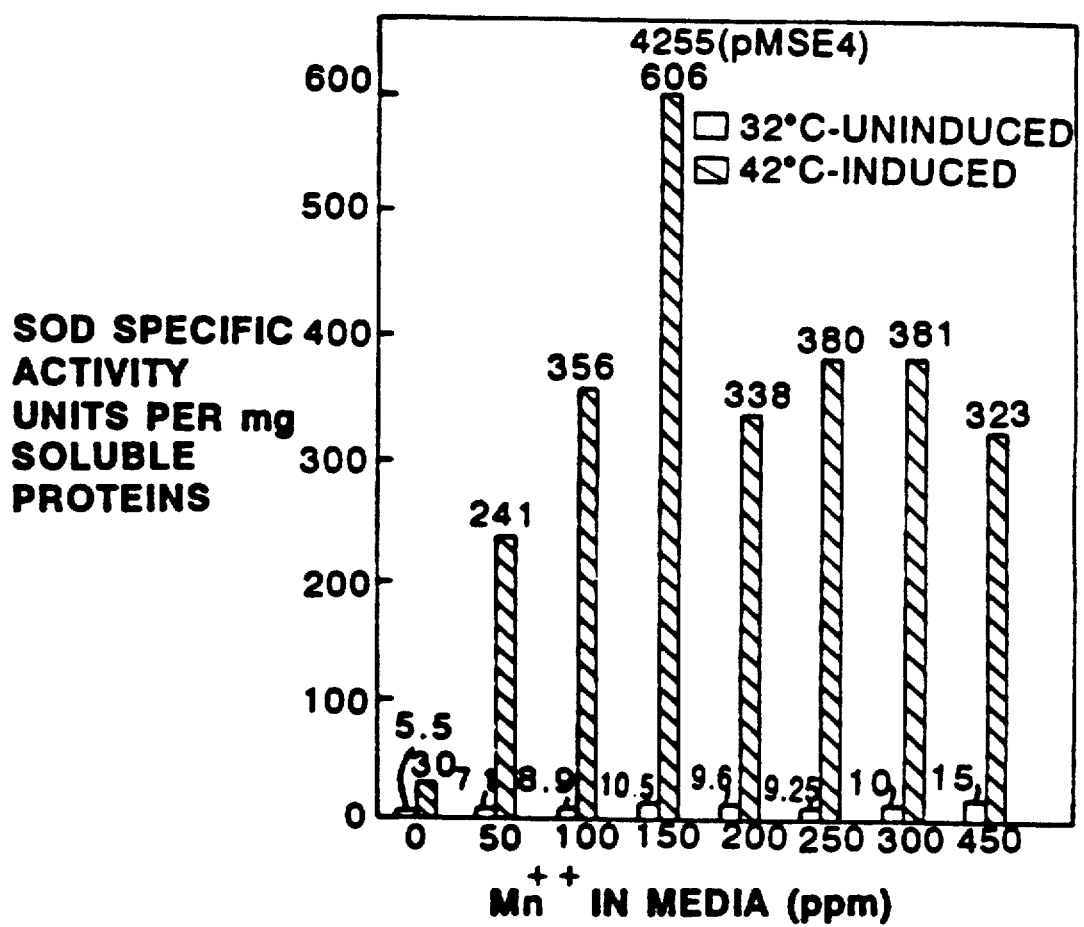

FIG. 3. Effect of $Mn^{++}$ Concentration on the Activity of SOD Produced in E. Coli The chart in FIG. 3 shows the correlation between the specific activity in units/mg of recombinant soluble MnSOD produced by E. coli strain A4255 containing plasmid pMSE-4 under both non-induction (32° C.) and induction (42° C.) conditions, and the concentration of $Mn^{++}$ (parts per million) in the growth medium.

Figure 4:
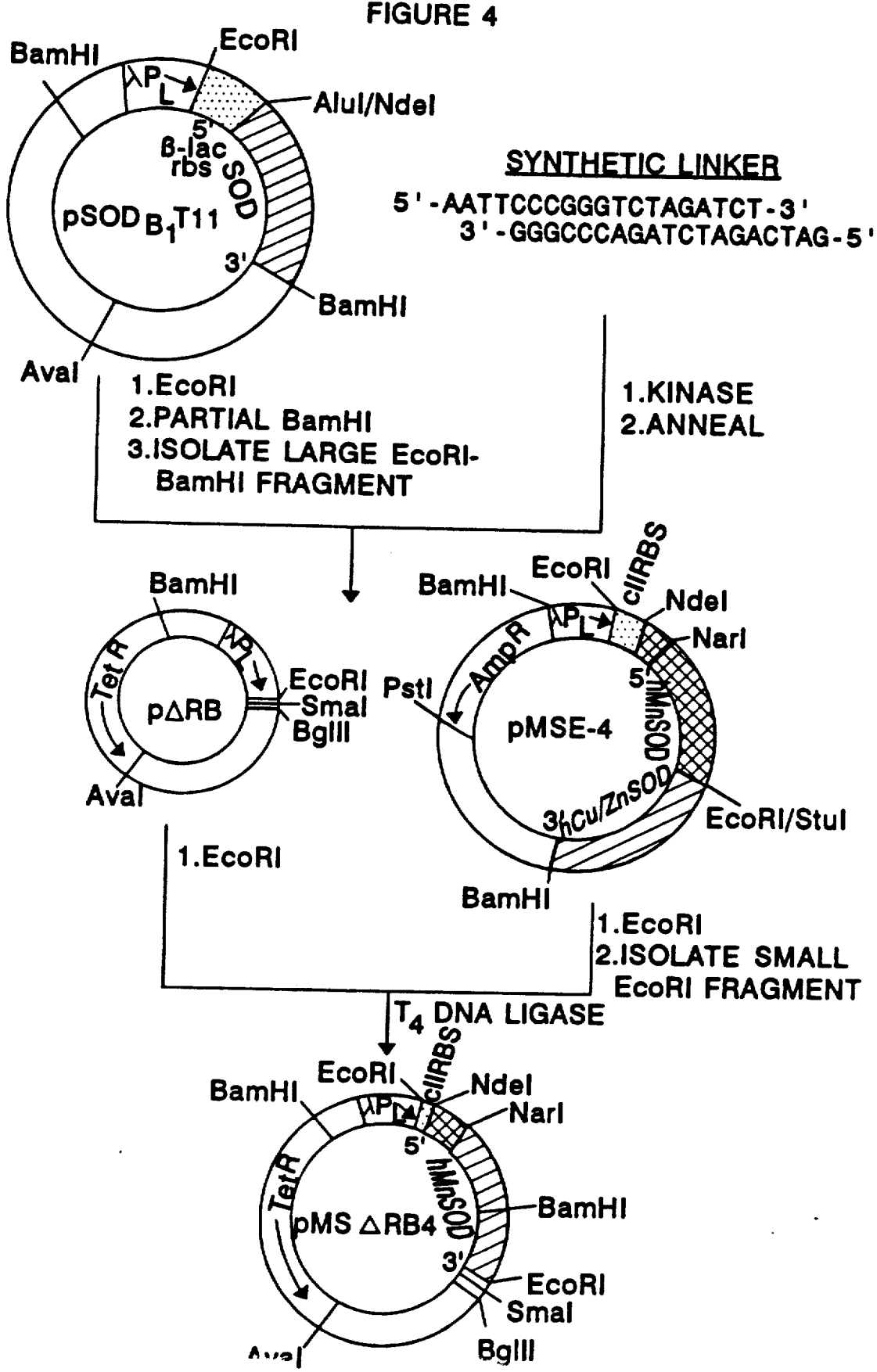

FIG. 4. Construction of pMSΔRB4: Human MnSOD Expression Plasmid $Tet^R$ expression vector, pΔRB, was generated from pSODβ$_1$T-11 by complete digestion with EcoRI followed by partial cleavage with BamHI restriction enzymes. pSODβ$_1$T-11 has been deposited with the American Type Culture Collection (ATCC) under Accession No. 53468. The digested plasmid was ligated with synthetic oligomer

5'- AATTCCCGGGTCTAGATCT - 3'

3'- GGGCCCAGATCTAGACTAG - 5' resulting in pΔRB containing the λ $P_L$ promoter.

The EcoRI fragment of MnSOD expression plasmid pMSE-4, containing cII ribosomal binding site and the complete coding sequence for the mature enzyme, was inserted into the unique EcoRI site of pΔRB. The resulting plasmid, pMSΔRB4, contains the MnSOD gene under control of λ $P_L$ and cII RBS and confers resistance to tetracycline.

Figure 5:
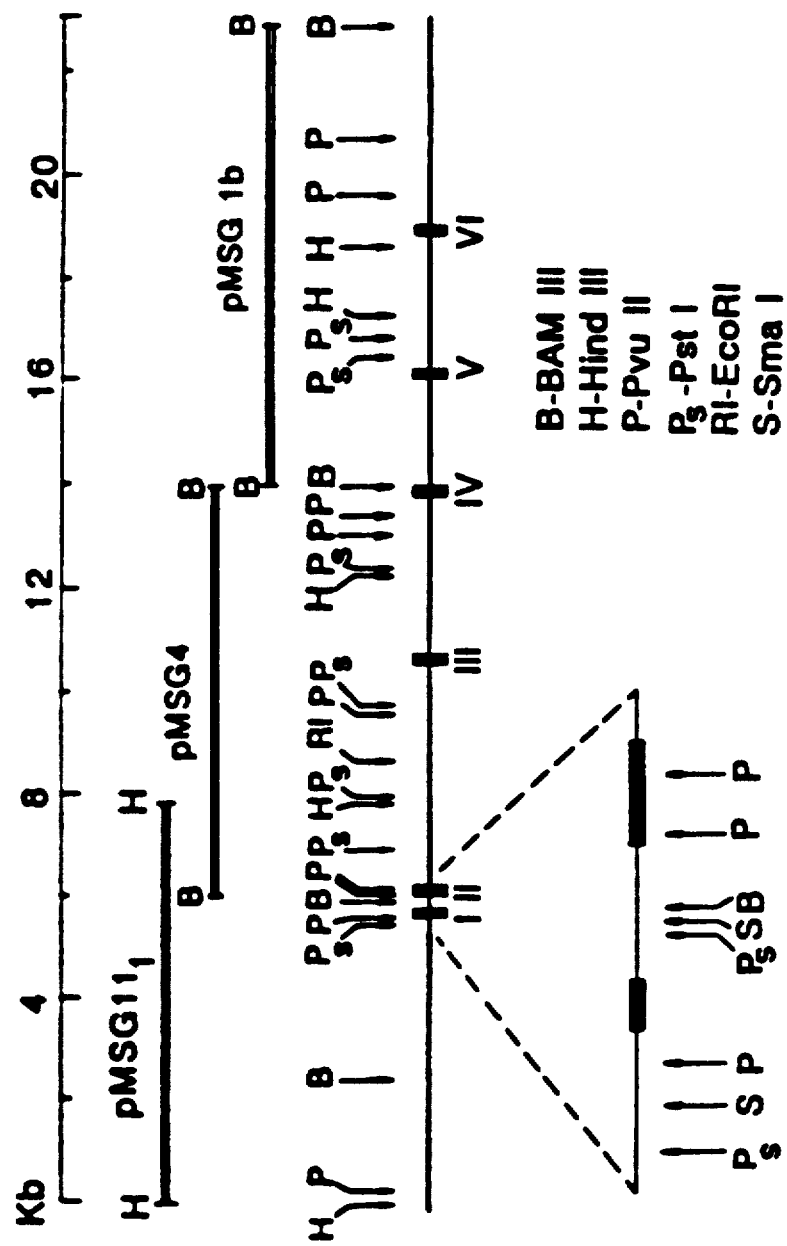

FIG. 5. Restriction Map and Organization of Human MnSOD Gene

The thick line represents genomic DNA with the positions of the various restriction endonucleases. The black boxes numbered I-VI are the exons. The three open bars above represent the genomic clones which contain the MnSOD gene.

FIG. 6A-6D. Nucleotide Sequence of Human MnSOD Gene

The coding regions and adjacent nucleotides are shown; the exons (shaded areas) were identified by comparison with the cDNA clones. The initator codon (ATG), termination codon (TAA) and the polyadenylation signal (AATAAA) are underlined. The Spl hexanucleotide (GGGCGG) binding site is indicated by a line above the sequence. Dotted arrows represent possible stem-loop structures; straight arrows are direct repeats. It should be noted that the numbers shown to the left of the Figure are arbitrary and were selected only to assist in the identification of the regions mentioned in the text. Neither the entire non-coding or the entire coding region is shown.

FIG. 7. Exon-Intron Junctions of Human MnSOD Gene

The nucleotide sequence at the borders of all five introns are compared with the consensus sequences. Note that a shift of one nucleotide in intron #1 may alter either the donor or acceptor sequences.

Figure 8:
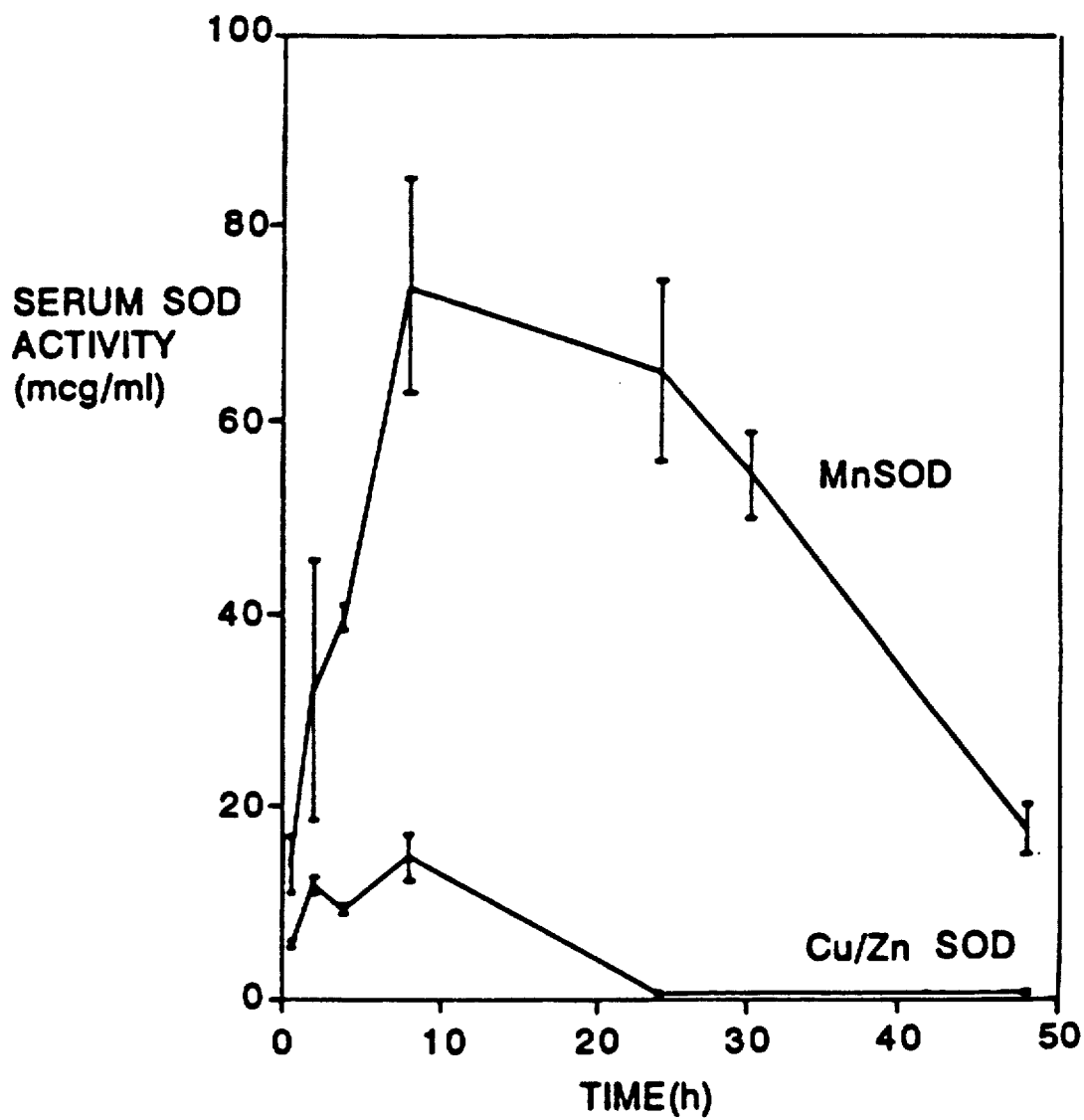

FIG. 8. Pharmacokinetics of MnSOD After Subcutaneous Injection Into Rats

Time course of the serum levels of SOD enzymatic activity in rats after subcutaneous administration of 50 mg/kg of CuZn SOD (lower curve) or MnSOD (upper curve). Values are expressed as the mean and standard error (3 rats per point) of the enzymatic activity, calculated as ug/ml assuming a specific activity of 3000 units/mg.

Figure 9:
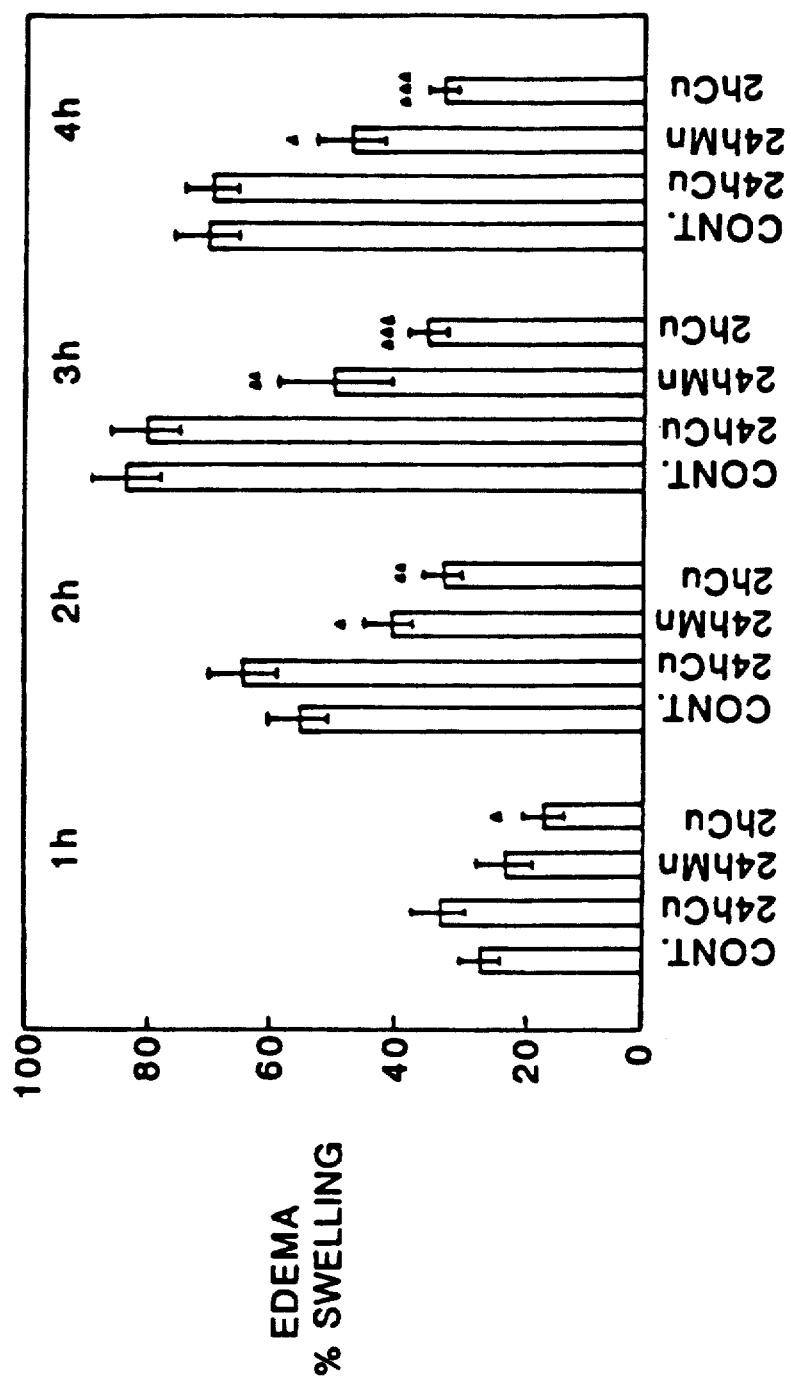

FIG. 9. Comparison Between MnSOD and CuZn SOD

Effect of CuZn SOD and MnSOD administration on carrageenan-induced paw swelling in rats. MnSOD (50 mg/kg) was administered subcutaneously 24 hours before carrageenan injection ($-24$ h Mn); CuZn SOD (50 mg/kg) was administered subcutaneously 2 hours ($-2$ h Cu) or 24 hours ($-24$ h Cu) prior to carrageenan injection. The control rats received carrageenan only. The bars and vertical brackets represent the means ±standard errors (8 rats per group) of the increase in paw volume 1, 2, 3 and 4 hours after carrageenan administration. The asterisks indicate the statistical significance of the difference between the treated groups compared to the control group: (*) $p<0.05$; () $p<0.01$; (*) $p<0.001$.

DETAILED DESCRIPTION OF THE INVENTION

A double-stranded DNA molecule which includes cDNA encoding human manganese superoxide dismutase polypeptide or an analog or mutant thereof has been isolated from a human T-cell cDNA library. The nucleotide sequence of a double-stranded DNA molecule which encodes human manganese superoxide dismutase polypeptide or an analog or mutant thereof has been discovered. The sequence of one strand of DNA molecule encoding the human manganese superoxide dismutase polypeptide or analog thereof is shown in FIG. 1 and includes nucleotides numbers 115 to 708 inclusive. The sequence of one strand encoding hMnSOD analog or mutant is substantially similar to the strand encoding the hMnSOD polypeptide. The nucleotide sequence of the prepeptide of human manganese superoxide dismutase is also shown in FIG. 1. Nucleotides numbers 43 through 114 inclusive code for this prepeptide.

The methods of preparing the cDNA and of determining the sequence of DNA encoding the human manganese superoxide dismutase polypeptide, analog or mutant thereof are known to those skilled in the art and are described more fully hereinafter. Moreover, now that the DNA sequence which encodes the human manganese superoxide dismutase has been discovered, known synthetic methods can be employed to prepare DNA molecules containing portions of this sequence.

Conventional cloning vehicles such as plasmids, e.g., pBR322, viruses or bacteriophages, e.g., can be modified or engineered using known methods so as to produce novel cloning vehicles which contain cDNA encoding human manganese superoxide dismutase polypeptide, or analogs or mutants thereof. Similarly, such cloning vehicles can be modified or engineered so that they contain DNA molecules, one strand of which includes a segment having the sequence shown in FIG. 1 for human manganese superoxide dismutase polypeptide or segments substantially similar thereto. The DNA molecule inserted may be made by various methods including enzymatic or chemical synthesis.

The resulting cloning vehicles are chemical entities which do not occur in nature and may only be created by the modern technology commonly described as recombinant DNA technology. Preferably the cloning vehicle is a plasmid, e.g. pMSE-4 or pMSΔRB4. These cloning vehicles may be introduced in cells, either procaryotic, e.g., bacterial (*Escherichia coli, B.subtilis,* etc.) or eukaryotic, e.g., yeast or mammalian, using techniques known to those skilled in the art, such as transformation, transfection and the like. The cells into which the cloning vehicles are introduced will thus contain cDNA encoding human manganese superoxide dismutase polypeptide or analog or mutant thereof if the cDNA was present in the cloning vehicle or will contain DNA which includes a strand, all or a portion of which has the sequence for human MnSOD polypeptide shown in FIG. 1 or sequence substantially similar thereto if such DNA was present in the cloning vehicle.

*Escherichia coli* are preferred host cells for the cloning vehicles of this invention. A presently preferred auxotrophic strain of *E. coli* is A1645 which has been deposited with the American Type Culture Collection in Rockville, Md., U.S.A. containing plasmid pApoE-Ex2, under ATCC Accession No. 39787. All deposits with the American Type Culture Collection referred to in this application were made pursuant to the Budapest Treaty on the International Recognition of the Deposit of Microorganisms.

A1645 was obtained from A1637 by selection for Gal+ (ability to ferment galactose) as well as loss of tetracycline resistance. It still contains elements of phage λ. Its phenotype is C600 r−m+ gal+ thr− leu− lacZ− bl (λcI857 ΔHl ΔBamHI N+).

A1637 was obtained from C600 by inserting transposon containing tetracycline resistance gene into the galactose operon as well as elements of phage λ including those elements responsible for cI repressor synthesis. C600 is available from the American Type Culture Collection, as ATCC Accession No. 23724.

Prototrophic strains of *Escherichia coli* which enable high level polypeptide expression even when grown in a minimal media are even more preferred as hosts for expression of genes encoding manganese superoxide dismutase. One presently preferred prototrophic strain is A4255. Strain A4255 containing the plasmid pMSE-4 has been deposited with the American Type Culture Collection under ATCC Accession No. 53250.

The resulting cells into which DNA encoding human manganese superoxide dismutase polypeptide or analog or mutant thereof has been introduced may be treated, e.g. grown or cultured as appropriate under suitable conditions known to those skilled in the art, so that the DNA directs expression of the genetic information encoded by the DNA, e.g. directs expression of the hMnSOD polypeptide or analog or mutant thereof, and the cell expresses the hMnSOD polypeptide or analog or mutant thereof which may then be recovered.

As used throughout this specification, the term "superoxide dismutase" (SOD) means an enzyme or a polypeptide acting upon superoxide or oxygen-free radicals as receptors, or which catalyze the following dismutation reaction:

$$2O_2^- + 2H^+ \rightarrow O_2 + H_2O_2$$

The term "manganese superoxide dismutase" (MnSOD) as used herein means any superoxide dismutase molecule containing the element manganese, in any of its chemical forms.

The term "human manganese superoxide dismutase polypeptide" as used herein means a polypeptide of 198 amino acids a portion of the amino acid sequence of which is shown in FIG. 1; the N-terminus of the sequence is the lysine encoded by nucleotides 115-117 of FIG. 1 and the COOH terminus of the sequence is the lysine encoded by nucleotides 706-708 of FIG. 1.

The term "polypeptide manganese complex" as used herein means a molecule which includes a human manganese superoxide dismutase polypeptide in a complex with manganese in any of its chemical forms and which has the enzymatic activity of naturally-occurring human manganese superoxide dismutase.

The term "human manganese superoxide dismutase" as used herein means a molecule which includes at least two human manganese superoxide dismutase polypeptides in a complex with manganese in any of its chemical forms and which has the enzymatic activity of naturally-occurring human manganese superoxide dismutase.

The term "human manganese superoxide dismutase polypeptide analog" as used herein means a polypeptide which includes a human manganese superoxide dismutase polypeptide to either or both ends of which one or more additional amino acids are attached.

The term "polypeptide manganese complex analog" as used herein means a molecule which includes a polypeptide manganese complex, the polypeptide portion of which includes one or more additional amino acids attached to it at either or both ends.

The term "human manganese superoxide dismutase analog" as used herein means a molecule that includes at least two polypeptides at least one of which is human manganese superoxide dismutase polypeptide analog, in a complex with manganese in any of its chemical forms, and which has the enzymatic activity of naturally-occurring human manganese superoxide dismutase.

The term "human manganese superoxide dismutase polypeptide mutant" as used herein means a polypeptide having an amino acid sequence substantially identical to that of the human manganese superoxide dismutase polypeptide but differing from it by one or more amino acids.

The term "polypeptide manganese complex mutant" means a molecule which includes a human manganese superoxide dismutase polypeptide mutant in a complex with manganese in any of its chemical forms and which has the enzymatic activity of manganese superoxide dismutase.

The term "human manganese superoxide dismutase mutant" as used herein means a molecule which includes at least two polypeptides at least one of which polypeptides is a human manganese superoxide dismutase polypeptide mutant in a complex with manganese in any of its chemical forms and which has the enzymatic activity of naturally-occurring human manganese superoxide dismutase.

The mutants of hMnSOD polypeptide and hMnSOD which are included as a part of this invention may be prepared by mutating the DNA sequence shown in FIG. 1, the N-terminus of which sequence is the lysine encoded by nucleotides 115-117 and the COOH terminus of which sequence is encoded by nucleotides 706-708.

The DNA may be mutated by methods known to those of ordinary skill in the art, e.g. Bauer et al., Gene 37: 73-81 (1985). The mutated sequence may be inserted into suitable expression vectors as described herein, which are introduced into cells which are then treated so that the mutated DNA directs expression of the hMnSOD polypeptide mutants and the hMnSOD mutants.

The enzymatically active form of human manganese superoxide dismutase is believed to be a protein having at least two, and possibly four, identical subunits, each of which has approximately 198 amino acids in the sequence shown in FIG. 1 for human manganese superoxide dismutase, the N-terminus of the sequence being the lysine encoded by nucleotides 115-117 of FIG. 1 and the COOH terminus of the sequence being the lysine encoded by nucleotides 706-708 of FIG. 1.

Human MnSOD or analogs or mutants thereof may be prepared from cells into which DNA or cDNA encoding human manganese superoxide dismutase, or its analogs or mutants have been introduced. This human MnSOD or analogs or mutants may be used to catalyze the dismutation or univalent reduction of the superoxide anion in the presence of protons to form hydrogen peroxide as shown in the following equation:

$$2O_2^- + 2H^+ \xrightarrow{\text{human MnSOD}} H_2O_2 + O_2$$

Veterinary and pharmaceutical compositions may also be prepared which contain effective amounts of hMnSOD or one or more hMnSOD analogs or mutant and a suitable carrier. Such carriers are well-known to those skilled in the art. The hMnSOD or analog or mutant thereof may be administered directly or in the form of a composition to the animal or human subject, e.g., to treat a subject afflicted by inflammations or to reduce injury to the subject by oxygen-free radicals on reperfusion following ischemia or organ transplantation. The hMnSOD or analog or mutant may also be added directly or in the form of a composition to the perfusion medium of an isolated organ, to reduce injury to an isolated organ by oxygen-free radicals on perfusion after excision, thus prolonging the survival period of the organ. Additionally, the hMnSOD or analog or mutant thereof may be used to reduce neurological injury on reperfusion following ischemia and to treat bronchial pulmonary dysplasia.

A method of producing enzymatically active human manganese superoxide dismutase or an analog or mutant thereof in a bacterial cell has also been discovered. The bacterial cell contains and is capable of expressing a DNA sequence encoding the human manganese superoxide dismutase or analog or mutant thereof. The method involves maintaining the bacterial cell under suitable conditions and in a suitable production medium. The production medium is supplemented with an amount of Mn++ so that the concentration of Mn++ in the medium is greater than about 2 ppm.

The bacterial cell can be any bacterium in which a DNA sequence encoding human manganese superoxide dismutase has been introduced by recombinant DNA techniques. The bacterium must be capable of expressing the DNA sequence and producing the protein product. The suitable conditions and production medium will vary according to the species and strain of bacterium.

The bacterial cell may contain the DNA sequence encoding the superoxide dismutase or analog in the body of a vector DNA molecule such as a plasmid. The vector or plasmid is constructed by recombinant DNA techniques to have the sequence encoding the SOD incorporated at a suitable position in the molecule.

In a preferred embodiment of the invention the bacterial cell is an *Escherichia coli* cell. A preferred auxotrophic strain of *E. coli* is A1645. A preferred prototrophic strain of *E. coli* is A4255 The *E. coli* cell of this invention contains a plasmid which encodes for human manganese superoxide dismutase or an analog or mutant thereof.

In a preferred embodiment of this invention, the bacterial cell contains the plasmid pMSE-4. A method of constructing this plasmid is described in the Description of the Figures and the plasmid itself is described in Example 2. This plasmid has been deposited with the ATCC under Accession No. 53250.

In another preferred embodiment of this invention, the bacterial cell contains the plasmid pMSΔRB4. A method of constructing this plasmid is described in the Description of the Figures and the plasmid itself is described in Example 5. This plasmid may be constructed from pSOD$\beta_1$T-11 which has been deposited with the American Type Culture Collection under Accession No. 53468.

In specific embodiments of the invention, an enzymatically active human manganese superoxide dismutase analog is produced by *E. coli* strain A4255 cell containing the plasmid pMSE-4 and by *E. coli* strain A4255 cell containing the plasmid pMSΔRB4.

The suitable production medium for the bacterial cell can be any type of acceptable growth medium such as casein hydrolysate or LB (Luria Broth) medium, the latter being preferred. Suitable growth conditions will vary with the strain of *E. coli* and the plasmid it contains, for example *E. coli* A4255 containing plasmid pMSE-4 is induced at 42° C. and maintained at that temperature from about 1 to about 5 hours. The suitable conditions of temperature, time, agitation and aeration for growing the inoculum and for growing the culture to a desired density before the production phase as well as for maintaining the culture in the production period may vary and are known to those of ordinary skill in the art.

The concentration of $Mn^{++}$ ion in the medium that is necessary to produce enzymatically active MnSOD will vary with the type of medium used.

In LB-type growth media $Mn^{++}$ concentrations of 150 ppm to 750 ppm have been found effective. It is preferred that in all complex types of growth mediums the concentration of $Mn^{++}$ in the medium is from about 50 to about 1500 ppm.

The specific ingredients of the suitable stock, culture, inoculating and production mediums may vary and are known to those of ordinary skill in the art.

This invention also concerns a method of recovering human manganese superoxide dismutase or analog or mutant thereof from bacterial cells which contain the same. The cells are first treated to recover a protein fraction containing proteins present in the cells including human manganese superoxide dismutase or analog or mutant thereof and then the protein fraction is treated to recover human manganese superoxide dismutase or analog or mutant thereof.

In a preferred embodiment of the invention, the cells are first treated to separate soluble proteins from insoluble proteins and cell wall debris and the soluble proteins are then recovered. The soluble proteins so recovered are then treated to separate, e.g. precipitate, a fraction of the soluble proteins containing the human manganese superoxide dismutase or analog or mutant thereof and the fraction is recovered. The fraction is then treated to separately recover the human manganese superoxide dismutase or analog or mutant thereof.

The following is a description of a more preferred embodiment of the invention. First, the bacterial cells are isolated from the production medium and suspended in a suitable solution having a pH of about 7.0 or 8.0. The cells are then disrupted and centrifuged. The resulting supernatant is heated for a period of about 30 to 120 minutes at a temperature between approximately 55° to 65° C., preferably for 45-75 minutes at 58° to 62° C. and more preferably one hour at 60° C., and then cooled to below 10° C., preferably to about 4° C. Any precipitate which may form during cooling is removed, e.g. by centrifugation and then the cooled supernatant is dialyzed against an appropriate buffer. Preferably the cooled supernatant is dialyzed by ultrafiltration employing a filtration membrane smaller than 30K, most preferably 10K. Appropriate buffers include 2 mM potassium phosphate buffer having a pH of about 7.8. After or simultaneously with this dialysis the cooled supernatant may optionally be concentrated to an appropriate volume, e.g. 0.03 of the supernatant's original volume has been found to be convenient. The retentate is then eluted on an anion exchange chromatography column with an appropriate buffered solution, e.g., a solution at least 20 mM potassium phosphate buffer having a pH of about 7.8. The fractions of eluent containing superoxide dismutase are collected, pooled and dialyzed against about 40 mM potassium acetate, pH 5.5. The dialyzed pooled fractions are then eluted through a cation exchange chromatography column having a linear gradient of about 40 to about 200 mM potassium acetate (KOAC) and a pH of 5.5. The peak fractions containing the superoxide dismutase are collected and pooled. Optionally the pooled peak fractions may then be dialyzed against an appropriate solution, e.g. water or a buffer solution of about 10 mM potassium phosphate having a pH of about 7.8.

The invention also concerns purified, i.e. substantially free of other substances of human origin, human manganese superoxide dismutase or analogs or mutants thereof produced by the methods of this invention. In particular, it concerns a human manganese superoxide dismutase analog having at least two polypeptides, at least one of which polypeptides has the amino acid sequence shown in FIG. 1, the N-terminus of which sequence is the lysine encoded by nucleotides 115-117 of FIG. 1 and the COOH terminus of which sequence is the lysine encoded by nucleotides 706-708 of FIG. 1 plus an additional methionine residue at the N-terminus (MethMnSOD). A preferred embodiment of this invention concerns purified Met-hMnSOD having a specific activity of 3500 units/mg.

The invention further concerns the ligation of human MnSOD gene fragments taken from various plasmids to yield a complete human MnSOD gene fragment which can be introduced into mammalian cells for the production of MnSOD. The various human MnSOD fragments isolated from the plasmids detail the nucleotide sequence of the genomic human MnSOD gene including coding and adjacent nucleotides as well as a restriction map and organization of the gene.

The genomic gene commences at nucleotide 479 which is the first nucleotide of the ATG starting codon and is underlined in FIG. 6. The TAA termination codon for the genomic gene is at nucleotides 2022-2024.

These numbers are arbitrary numbers merely to assist in identifying the nucleotide region.

A restriction map and organization of the genomic human MnSOD gene is depicted in FIG. 5.

As noted, portions of genomic MnSOD DNA are found in each of three different clones, pMSG11-1, pMSG4, and pMSG-1b also depicted in FIG. 5 and the DNA from these clones was used to map the nucleotide sequence of FIG. 6.

Also shown in FIGS. 6 and 7 are the exon and intron regions of the human MnSOD gene.

This human MnSOD gene may be inserted into a plasmid which may in turn be inserted into a eucaryotic cell capable of expressing the human gene. Methods for recovery and purification of the protein are also contemplated similar to those discussed above.

EXAMPLES

The Examples which follow are set forth to aid in understanding the invention but are not intended to, and should not be construed to, limit its scope in any way. The Examples do not include detailed descriptions for conventional methods employed in the construction of vectors, the insertion of genes encoding polypeptides into such vectors or the introduction of the resulting plasmids into hosts. The Examples also do not include detailed description for conventional methods employed for assaying the polypeptides produced by such host vector systems or determining the identity of such polypeptides by activity staining of isoelectric focusing (IEF) gels. Such methods are well-known to those or ordinary skill in the art and are described in numerous publications including by way of example the following:

T. Maniatis, E. F. Fritsch and J. Sambrook, *Molecular Cloning: A Laboratory Manual*, Cold Spring Harbor Laboratory, New York (1982).

J. M. McCord and I. Fridovich, *J. Biol. Chem.* 244:6049-55 (1969).

C. Beauchamp and I. Fridovich, *Anal. Biochem.* 44:276-87 (1971).

EXAMPLE 1

In order to identify MnSOD cDNA clones, mixed oligomer probes were synthesized according to the published amino acid sequence (18,19).

5'-probe - 30 mer sequence from $AA_{15}-AA_{24}$ (18,19)

```
5'                                   3'
TTGCATAATTTGTGCCTTAATGTGTGGTTC
      T    . G         T        G
      G         G
```

3'-probe - 32 mer sequence from $AA_{179}-AA_{189}$ (19)

```
5'                                     3'
TCTGTTACGTTTTCCCAGTTTATTACGTTCCA
     G  G                    G  G
```

The 5'-probe consisting of 30 nucleotides corresponds to amino acids 15 to 24 of mature MnSOD. The 3'-probe consisting of 32 nucleotides corresponds to amino acids 179 to 189 of mature MnSOD. The 5'-probe is a mixed probe consisting of 36 different sequences, as shown above. The 3'-probe is a mixed probe consisting of 16 different sequences as shown above. (When more than one nucleotide is shown at a given position, the DNA strand was synthesized with equimolar amounts of each of the shown nucleotides thus resulting in the mixed probe).

The 5'-probe was employed to screen 300,000 plaques of a T-cell cDNA library cloned into the gt-10 vector. Hybridization to phage plaque replicas immobilized on nitrocellulose filters was performed according to standard procedures (Maniatis et al. supra) except that the hybridization was performed at 50° C. in 8xSSC for 16 hrs. The filters were then washed at 50° C. with 5xSSC and 0.1% SDS. Three positive plaques were isolated and named Phi MS8, Phi MS1 and Phi MS1J.

EcoRI digests of DNA from Phi MS8 and Phi MS1 showed that they both have cDNA inserts approximately 800 bp long, which hybridize to both the 5' and 3' oligonucleotide probes. Phi MS1J carried only 450 bp cDNA insert which hybridized only to the 5' end probe.

The EcoRI inserts of the three phage clones were subcloned into the EcoRI site of pBR322 thus yielding pMS8-4, pMS1-4 and pMS1J, respectively. Restriction analysis and hybridization to the 5' and 3' oligonucleotide probes revealed similar patterns for both pMS8-4 and pMS1-4. The following restriction map showing the 5'→3' orientation has been deduced for both plasmids.

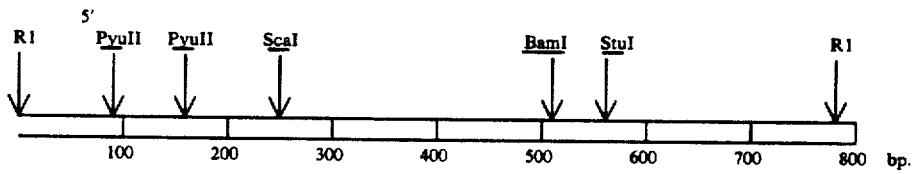

The sequence of the cDNA insert of pMS8-4 is shown in FIG. 1. The predicted amino acid sequence differs from the published amino acid sequence (19) in that Glu appears instead of Gln in three (3) locations (AA 42, 88, 109) and an additional two amino acids, Gly and Trp appear between $AA_{123-124}$. Sequence analysis of pMS1-4 and pMS1J revealed that the three MnSOD clones were independently derived and confirmed these differences from the published amino acid sequence.

The sequence upstream of the N-terminal Lysine of mature MnSOD predicts a pre-peptide sequence of 24 amino acids.

EXAMPLE 2

Construction of pMSE-4: $Amp^R$ Human MnSOD Expression Plasmid

The starting point for the construction of pMSE-4 is the plasmid pMS8-4 which was obtained as described in Example 1. Plasmid pMS8-4, containing human MnSOD cDNA on an EcoRI insert, was digested to completion with NdeI and NarI restriction enzymes. The large fragment was isolated and ligated with a synthetic oligomer as depicted in FIG. 2. The resulting plasmid, pMS8-NN contains the coding region for the mature MnSOD, preceded by an ATG initiation codon. The above plasmid was digested with EcoRI, ends were filled in with Klenow fragment of Polymerase I and further cleaved with NdeI. The small fragment containing the MnSOD gene was inserted into pSODα 13 which was treated with NdeI and StuI. pSODα 13 may be obtained as described in pending, co-assigned U.S. patent application Ser. No. 644,245, filed Aug. 27, 1984 which is hereby incorporated by reference. This generated plasmid pMSE-4 containing the MnSOD coding region preceded by the cII ribosomal binding site and under the control of λ $P_L$ promoter. Plasmid pMSE-4 has been deposited with the American Type Culture Collection under ATCC Accession No. 53250. All methods utilized in the above processes are essentially the same as those described in Maniatis, supra.

EXAMPLE 3

Expression of the Recombinant Human MnSOD

Plasmid pMSE-4 was introduced into *Escherichia coli* strain A4255 using known methods. Then the *E. coli* strain 4255, containing pMSE-4, were grown at 32° C. in Luria Broth (LB) medium containing 100 μg/ml of ampicillin until the Optical Density (OD) at 600 nm was 0.7. Induction was performed at 42° C. Samples taken at various time intervals were electrophoresed separated on sodium dodecyl sulfate - polyacrylamide gels electrophoresis (SDS-PAGE). The gels showed increases in human MnSOD levels up to 120 minutes post-induction, at which stage the recombinant MnSOD protein comprised 27% of total cellular proteins as determined by scanning of Coomassie-blue stained gel. Sonication of samples for 90 sec. in a W-375 sonicator and partitioning of proteins to soluble (s) and non-soluble (p) fractions by centrifugation at 10,000 g for 5 min. revealed that most of the recombinant MnSOD produced was non-soluble. The induced soluble protein fraction contained only slightly more SOD activity than the uninduced counterpart, as assayed by standard methods. The standard assay is performed in 3 ml of 0.05M potassium phosphate buffer at pH 7.8 containing $10^{-4}$M EDTA in a 1.0 cm cuvette thermostatted at 25° C. The reaction mixture contained $1 \times 10^{-5}$M ferricytochrome c, $5 \times 10^{-5}$M xanthine, and sufficient xanthine oxidase to produce a rate of reduction of ferricytochrome c at 550 nm of 0.025 absorbance units per minute. The concentration of xanthine oxidase in the cuvette was usually $6 \times 10^{-9}$M but may vary with different preparations of the enzyme. Under these defined conditions, the amount of superoxide dismutase required to inhibit the rate of reduction of cytochrome c by 50% (i.e. to a rate of 0.0125 absorbance units per minute) is defined as 1 unit of activity. See McCord et al., supra. Apparently a portion of the MnSOD found in the soluble fraction is inactive. This suggested that most of the human MnSOD produced under the conditions described in this Example is, in effect, inactive.

EXAMPLE 4

Effect of $Mn^{++}$ in Growth Media on MnSOD Solubility and Activity

The addition of $Mn^{++}$ in increasing concentrations up to 450 ppm to the growth media of *E. coli* A4255, containing pMSE-4, prior to a 2 hr. induction at 42° C., at OD 600=0.7, had no adverse effect on the overall yield of human MnSOD. Analysis of sonicated protein fractions soluble (s) and non-soluble (p) on sodium dodecyl sulfate - polyacrylamide gel electrophoresis (SDS-PAGE), showed increased solubilization of the recombinant protein with increased $Mn^{++}$ concentrations (Table 1). An assay of SOD activity (see McCord et al., supra) suggests a correlation between increased $Mn^{++}$ concentrations in the growth media and increased solubility of the MnSOD with an apparent optimum at 150 ppm $Mn^{++}$ concentration in the media (FIG. 3). Furthermore increased $Mn^{++}$ concentrations activated previously inactive soluble enzyme. Soluble protein fractions of induced cultures grown at these $Mn^{++}$ levels show up to 60-fold increase in SOD activity over soluble protein fractions of non-induced cultures grown at these $Mn^{++}$ levels. Activity staining of isoelectric focusing (IEF) gels (see Beauchamp et al, supra.) revealed that multi forms of the recombinant MnSOD were identical to those of native human liver MnSOD.

Results for human MnSOD production by *E. coli* A1645 containing pMSE-4 were similar to those described above.

TABLE 1

| $Mn^{++}$ (ppm) | Percent Soluble human Mn SOD of Total human MnSOD Induced | Percent Soluble human Mn SOD of Soluble Bacterial Proteins | Specific Activity units/mg Soluble Proteins |
|---|---|---|---|
| 0 | 30.6 | 7.2 | 30 |
| 50 | 72.7 | 15.4 | 241 |
| 100 | 78.0 | 16.9 | 356 |
| 150 | 82.9 | 18.8 | 606 |
| 200 | 82.0 | 20.8 | 338 |
| 250 | 79.2 | 20.4 | 380 |
| 300 | 80.8 | 20.3 | 381 |
| 450 | 89.2 | 22.4 | 323 |

EXAMPLE 5

Construction of pMSΔRB4: $Tet^R$ Human MnSOD Expression Plasmid $Tet^R$ expression vector, pΔRB, was generated from pSODβ₁T-11 by complete digestion with EcoRI followed by partial cleavage with BamHI restriction enzymes. pSODβ₁T-11 has been deposited with the American Type Culture Collection under Accession No. 53468. The digested plasmid was ligated with synthetic oligomer

5'- AATTCCCGGGTCTAGATCT - 3'

3'- GGGCCCAGATCTAGACTAG - 5' resulting in pΔRB containing the λ $P_L$ promoter.

The EcoRI fragment of MnSOD expression plasmid pMSE-4, containing cII ribosomal binding site and the complete coding sequence for the mature enzyme, was inserted into the unique EcoRI site of pΔRB. The resulting plasmid, pMSΔRB4, contains the MnSOD gene under control of λ $P_L$ cII RBS and confers resistance to tetracycline (FIG. 4).

EXAMPLE 6

Expression of Human MnSOD from pMSΔRB4

Plasmid pMSΔRB4 was introduced into *Escherichia coli* strain A4255, using known methods. Cultures were grown at 32° C. in Luria Broth (LB) containing various concentrations of Mn++, until the Optical Density (OD) at 600 nm reached 0.7. Induction was performed at 42° C. Samples taken at various time intervals were electrophoresed on SDS-PAGE. hMnSOD level increased with induction time up to 120 minutes, at which stage it comprised about 15% of total cellular proteins as determined by scanning of Coomassie Blue stained gel.

The induced MnSOD was soluble, regardless of Mn++ concentration in growth media. This is in contrast with observations for the Amp$^R$ plasmid pMSE-4. (See Example 4.) However, maximum SOD activity and expression level were dependent on Mn++ supplementation (Table 2).

TABLE 2

| | MnSOD Expression in *E.Coli* A4255 (pMSΔRB4) | | |
|---|---|---|---|
| ppm Mn++ | Percent Soluble hMnSOD of Soluble Bacterial Proteins 42° | Specific Activity Units/mg Soluble Proteins 32° | 42° |
| 0 | 10.9 | 8.0 | 23 |
| 50 | 19.8 | 8.0 | 227 |
| 100 | 16.0 | 8.0 | 241 |
| 200 | 17.0 | 10.0 | 278 |
| 300 | 16.0 | 9.3 | 238 |

EXAMPLE 7

Purification of Enzymatically Active Recombinant Human MnSOD

*E. coli* strain A4255 harboring plasmid pMSΔRB4 was fermented in LB supplemented with 750 ppm Mn++, at 32° C. to an OD600 of 17.0. Induction of human MnSOD expression was effected by a temperature shift to 42° C. for 2 hours at which stage the culture reached A600 of 43.0. Cells were harvested by centrifugation and resuspended in 0.2 original volume in 50 mM potassium phosphate buffer, pH 7.8 containing 250 mM NaCl. Bacteria were disrupted by a double passage through Dynomill, centrifuged and cell debris were discarded. The supernatant was heated for 1 hour at 60° C., cooled to 4° C. and the cleared supernatant was concentrated to 0.03 original volume and dialyzed against 2 mM potassium phosphate buffer, pH 7.8, on a Pellicon ® ultra filtration unit equipped with a 10K membrane. The crude enzyme preparation was loaded onto a DE52 column, washed thoroughly with 2 mM potassium phosphate buffer, pH 7.8 and eluted with 20 mM potassium phosphate buffer, pH 7.8. Pooled fractions containing the enzyme were dialyzed against 40 mM potassium acetate, pH 5.5, loaded onto a CM52 column and eluted with a linear gradient of 40–200 mM potassium acetate, pH 5.5. Peak fractions containing human MnSOD were pooled, dialyzed against H$_2$O, adjusted to 10 mM potassium phosphate buffer, pH 7.8 and frozen at −20° C.

Recombinant human MnSOD obtained was more than 99% pure, with a specific activity of about 3500 units/mg. The overall yield of the purification procedure was about 30% (Table 3).

Sequencing of the purified enzyme shows the presence of an additional methionine at the N-terminal amino acid as compared with the known human MnSOD (19).

Analysis for metal content by atomic absorption revealed about 0.77 atoms Mn per enzyme subunit. This is in accordance with published data (23).

TABLE 3

| | Purification of Recombinant Human* Mn-SOD | | | |
|---|---|---|---|---|
| | Total Proteins | Yield | | Specific Activity |
| Step | gm | gmSOD | % | units/mg |
| Dynomill supernatant | 100.0 | 11.9 | 100.0 | 417 |
| 60° C. supernatant | 24.0 | 8.2 | 68.9 | 1197 |
| Pelicon retentate | 20.0 | 7.5 | 63.0 | 1350 |
| DE52 eluate | 7.3 | 5.7 | 48.0 | 2732 |
| CM52 eluate | 4.2 | 4.2 | 35.3 | 3500 |

*Values for enzyme purified from 15 L fermentation.

EXAMPLE 8

Isolation and Structure of Human MnSOD Gene

Human placental DNA digested with HindIII and BamHI was fractionated according to its size, hybridized with an MnSOD cDNA probe and the positive enriched fractions were cloned in pBR322. Three distinct clones were identified according to their restriction and hybridization patterns: pMSG11-1, overlapping pMSG4, both comprising the 5' end of MnSOD gene and followed by the consecutive clone pMSG-1b which contains the 3' end of the gene. Plasmid pMSG11-1 has been deposited in the ATCC under Accession No. 67363; plasmid pMSG4 has been deposited in the ATCC under Accession No. 67364; and plasmid pMSG-1b has been deposited in the ATCC under Accession No. 67365. FIG. 5 shows the restriction map and organization of the MnSOD gene. The nucleotide sequence of the gene is shown in FIG. 6. The MnSOD gene spans a region of about 15 Kb and contains six exons. The first intron interrupts the region coding for the leader peptide while the last intron appears in the 3' untranslated region downstream to the TAA termination codon.

The sequences of the donor and acceptor spl ice junctions at the exon-intron boundries are summarized in FIG. 7 and compared with the consensus sequence. It should be pointed out that the first intron contains either an unusual donor sequence; GG instead of the highly conserved GT (as depicted in FIG. 6), or an unusual acceptor sequence; GG instead of AG (if one moves the exon by one nucleotide). All other four introns are bound by the conserved GT . . . AG nucleotides.

The promoter region lacks TATA and/or CAT boxes. However, it is highly rich in GC and contains eight repeats of the consensus hexanucleotide core for binding transcription factor Spl (GGGCGG). Moreover, it includes a series of direct repeats and possible stem-loop structures. The polyadenylation signal AATAAA appears 85 nucleotides downstream from the last exon (according to the known cDNA sequence). The sequence of the promoter region and the sequence of the coding regions and adjacent nucleotides was determined.

The MnSOD gene regions from plasmids pMSG11-1, pMSG4 and pMSG-1b can be conveniently isolated from the plasmids and ligated to one another to form the entire MnSOD gene. For example, the approximately 6 KB HindIII-partial BamHI fragment from pMSG11-1 can be ligated to the entire BamHI insert in plasmid pMSG4 followed by ligation to the entire BamHI insert from pMSG-1b. The result of this ligation would be a DNA fragment encoding the human MnSOD gene. This DNA fragment could then be introduced into mammalian cells through known methods either directly or after ligation to a cloning vehicle such as a plasmid or virus. The transformed cell line could then be used for production of MnSOD polypeptide, analog or mutant thereof, by culturing in a suitable medium under suitable conditions. The polypeptide so produced could then be recovered by methods similar to those set forth in Example 7. The polypeptide so recovered could then be used formulated and used therapeutically, for example, for treatment of ischemia or inflammation.

EXAMPLE 9

Transcription of MnSOD in Human Cells

The human MnSOD cDNA from plasmid pMS-84 (FIG. 2) was hybridized to polyA+ RNA from human cell lines, human placenta, mouse WEHI-3 cells and bovine liver. Two species of human mRNA for MnSOD were identified, a major transcript of human mRNA encoding MnSOD of about 1000 nucleotides (nt) long and a minor transcript of about 4000 nt in length. The mouse mRNA for MnSOD is similar in size to the human major transcript, whereas mRNA for bovine MnSOD is about 300 nt longer. The long human trancript (4000 nucleotides) hybridizes to the fifth intron of the human MnSOD gene, downstream from the exon coding for the carboxy terminus of the enzyme. This partially spliced transcript is non-tissue specific.

The proportion of both CuZn and MnSOD mRNAs in various cell lines was in the order of $10^{-3}$%, as determined by hybridization of the SOD cDNA probes to dot blots of serially diluted polyA+ RNA (Table IV). The MnSOD message was most abundant in Hepatoma cells ($2.5 \times 10^{-3}$%) and CuZn SOD transcripts were most abundant in the T-lymphocyte line ($4 \times 10^{-3}$%).

TABLE IV

| Transcription Levels of MnSOD and CuZn SOD in Human Cell Lines % of polyA+ RNA | | |
|---|---|---|
| Cell Line | MnSOD | CuZnSOD |
| 1. PEER T-cell | $0.6 \times 10^{-3}$ | $4.0 \times 10^{-3}$ |
| 2. 5637 Bladder Carcinoma | $0.8 \times 10^{-3}$ | $1.6 \times 10^{-3}$ |
| 3. Alexander Hepatoma | $2.5 \times 10^{-3}$ | $2.0 \times 10^{-3}$ |

EXAMPLE 10

Pharmacokinetic and Anti-Inflammatory Properties of Human Recombinant Human MnSOD

INTRODUCTION

The anti-inflammatory activity of CuZn SOD has been demonstrated in various biological models. The pharmokinetics of CuZn SOD after administration by various routes has also been examined, and it has been found to have a relatively short half-life (approximately 7 minutes when injected intravenously). By contrast, very little is known about the pharmacokinetics and biological activity of MnSOD. There is only one report on the comparison of the pharmokinetic and anti-inflammatory properties of the CuZn and the Mn containing enzymes (Baret et al., 1984). Baret et al. claim that the half-life of MnSOD injected intravenously is extremely long (6.45 hours). On the other hand, MnSOD was shown to be ineffective against carrageenan-induced paw inflammation in rats, while the CuZn SOD was effective in reducing inflammation. In the study described herein, we have compared the pharmacokinetic properties of recombinant human MnSOD with that of a recombinant human CuZn SOD analog when given subcutaneously. Concurrently, we have compared the anti-inflammatory activities of these two enzymes in the carrageenan paw edema model. Unexpectedly, it was found that MnSOD was efficacious in reducing inflammation in the rat model system.

PHARMACOKINETIC STUDIES

Rats were injected subcutaneously with 50 mg/kg body weight of either recombinant human CuZn SOD analog or recombinant human MnSOD. Blood samples were drawn 0.5, 2, 4, 8, 24, 30 and 48 hours after injection and superoxide dismutase activity in the samples was determined by an enzymatic assay (Fridovich).

FIG. 8 summarizes the results. As shown, CuZn SOD analog values reached a maximum of about 10 ug/ml after 2 hours and stayed at about that level for additional 6 hours, but dropped to pre-injection levels after 24 hours. By contrast, MnSOD levels gradually increased to reach a maximal level of about 70 ug/ml by 8 hours, and stayed at about this level for at least 30 hours. By 48 hours, the enzyme activity in serum dropped to about 20 ug/ml, a value that was still well above the pre-injection levels.

ANTI-INFLAMMATORY ACTIVITY

The rat model of carrageenan-induced paw edema was used to assay the anti-inflammatory activity of CuZn SOD analog and MnSOD. In this model, Wistar-derived male rats (130-150g b.w.) were given a subplantar injection of 0.1 ml of 0.1% w/v carrageenan into the left hind paw. The paw volume was measured by an Hg-displacement volumeter (a modification of a Ugo-Basile volumeter, Comerio, Italy) before and at hourly intervals after paw injection. Animals were divided into 4 groups (8 rats/group). One group received a subcutaneous injection of 50 mg/kg of MnSOD 24 hours before carrageenan administration (−24 h Mn; cf. FIG. 9). The second group was injected with Cu/Zn SOD analog (50 mg/kg) 24 hours before the carrageenan challenge (−24 h Cu), while the third group was injected with 60 mg/Kg of CuZn SOD analog only 2 hours before the challenge (−2h Cu). The fourth group did not receive any pretreatment and served as a control.

The results are shown in FIG. 9. As seen, the administration of CuZn SOD analog 2 hours before the induction of inflammation resulted in a 50% reduction of the swelling response. In contrast, pretreatment with the CuZn enzyme 24 hours before challenge was without effect. However, a 24-hour pretreatment with MnSOD resulted in an anti-inflammatory response which was similar to the effect of the 2 hours pretreatment with CuZn SOD analog.

CONCLUSIONS

It has been demonstrated herein that the rate of disappearance of recombinant human MnSOD in the rat is much lower than that of the recombinant CuZn SOD analog. This is in agreement with the previous report of Baret et al. (1984) concerning the natural human MnSOD. However, the manganese-containing enzyme has been shown herein to be active in vivo as an anti-inflammatory agent—an activity that is attributed to its superoxide dismutase ability. This finding is surprising in view of the report of Baret et al. (1984), which claimed that MnSOD was not active in a similar system. The finding that MnSOD remains efficacious as an anti-inflammatory drug even 24 hours after administration indicates that it may be used as a long-acting therapeutic agent.

REFERENCES

1. McCord, J. M. and Fridovich, I., J. Biol. Chem. 244: 6049-55 (1969).
2. Fridovich, I. in *Advances in Inorganic Biochemistry*, eds. Eichhorn, G. L. and Marzilli, L. G. (Elsevier/North Holland, N.Y.), pp. 67-90 (1979).
3. Freeman, B. A. and Crapo, J. D., Laboratory Investion 47: 412-26 (1982).
4. Steinman, H. M. in *Superoxide Dismutase*, ed. Oberley, L. W. (CRC Press, Florida), pp. 11-68 (1982).
5. Hartz, J. W. and Deutsch, H. F., J. Biol. Chem. 247: 7043-50 (1972).
6. Jabusch, J. R., Farb, D. L., Kerschensteiner, D. A. and Deutsch, H. F., Biochemistry 19: 2310-16 (1980).
7. Barra, D., Martini, F., Bannister, J. V., Schinina, M. W., Rotilio, W. H., Bannister, W. H. and Bossa, F., FEBS Letters 120: 53-56 (1980).
8. Lieman-Hurwitz, J., Dafni, N. Lavie, V. and Groner, Y., Proc. Natl. Acad. Sci. USA 2808-11 (1982).
9. Sherman, L., Dafni, N., Lieman-Hurwitz, J. and Groner, Y., Proc. Natl. Acad. Sci. USA 80: 5465-69 (1983).
10. Oberley, L. W. and Buettner, G. R., Cancer Research 39: 1141-49 (1979).
11. Huber, W. and Menander-Huber, K. B., Clinics in Rheum. Dis. 6: 465-98 (1980).
12. McCord, J. M. and Roy, R. S., Can. J. Physiol. Pharma. 60: 1346-52 (1982).
13. Alvarez, J. G. and Storey, B. T., Biol. Reprod. 28: 1129-36 (1983).
14. Talmasoff, J. M., Ono, T. and Cutler, R. G., Proc. Natl. Acad. Sci. USA 77: 2777-81 (1980).
15. Lowry, O. H., Rosebrough, N. J., Farr, A. L. and Randall, R. J., J. Biol. Chem. 193: 265-75 (1951).
16. Weser, U. and Hartmann, H. J. 17: 78-80 (1971).
17. Jewett, S. LO., Latrenta, G. S. and Beck, C. M., Arc. Biochem. Biophys. 215: 116-128 (1982).
18. Harris, J. I. and Steinman, H. M., *Superoxide and Superoxide Dismutase*, Michelson, A. M., McCord, J. M. and Fridovich, I. eds., Academic Press, London, pp. 225-230 (1977).
19. Barra, D., Schinina, M. E., Simmaco, M., Bannister, J. V., Bannister, W. H., Rotilio, G. and Bossa, F., J. Biol. Chem. 259: 12595-601 (Oct. 25, 1984).
20. Baret, A., Jadot, G., and Michelson, A. M., Biochemical Pharmacology 33: 2755-60 (Sep. 1, 1984).
21. McCord, J. M. and Salin, M. L., *Movement, Metabolism and Bactericidal Mechanisms of Phagocytes*, Ross, A., Patriarca, P. L., Romeo, D. (eds) pp. 257-264 (1977).
22. Touati, D., Journal of Bacteriology 155: 1078-87 (1983).
23. McCord, J. M., Boyle, J. A., Day, Jr., E. D., Rizzolo, L. J. and Salin, M. L., *Superoxide and Superoxide Dismutase*, Michaelson, A. M., McCord, J. M., and Fridovich, I. (eds) Academic Press, London pp. 129-138 (1977).
24. European Patent Publication No. 0131843 A1, published Jan. 23, 1985, corresponding to European Patent Application No. 84107717.5, filed July 3, 1984, which claims priority of U.S. Ser. No. 514,188, filed Jul. 15, 1983.
25. Hallewell, et al., Nucleic Acids Res. 5: (1985).
26. European Patent Publication 0138111 A1, published Apr. 24, 1985, corresponding to European Patent Application No. 84111416.8, filed Sep. 25, 1984, which claims priority of U.S. Ser. No. 538,607, filed Oct. 3, 1983, and U.S. Ser. No. 609,412, filed May 11, 1984.
27. Journal 4(1): 77-84 (January, 1985).
28. Abstracts of the Fourth International Conference on Superoxide and Superoxide Dismutase, Rome, Italy, Sep. 1-6, 1985.

What is claimed is:

1. A plasmid for expression in a suitable *E. coli* host cell of a human manganese superoxide dismutase analog having the enzymatic activity of naturally-occurring human manganese superoxide dismutase, wherein the analog consists essentially of at least two non-covalently linked identical polypeptides, each such polypeptide consisting of 199 amino acids, the sequence of each such polypeptide having methionine at its N-terminus immediately adjacent to the lysine encoded by nucleotides 115-117 of FIG. 1 and continuing to the lysine encoded by nucleotides 706-708 of FIG. 1, which is the COOH terminus of the polypeptide, such plasmid comprising DNA encoding such polypeptide and suitable regulatory elements arranged within the plasmid so as to permit expression of the polypeptide and formation of the human manganese superoxide dismutase analog in the host cell.

2. A plasmid of claim 1 designated pMSE-4 deposited in *Escherichia coli* strain A4255 under ATCC Accession No. 53250.

3. A plasmid of claim 1 designated pMSΔRB4.

4. An *Escherichia coli* host cell into which the plasmid of claim 1 has been introduced.

5. An *Escherichia coli* cell of claim 4 containing the plasmid designated pMSE-4 and deposited under ATCC Accession No. 53250.

6. An *Escherichia coli* cell of claim 4 containing the plasmid designated pMSΔRB4.

7. A method of producing a human manganese superoxide dismutase analog which comprises growing the host plasmid system of claim 4 under conditions permitting production of the human manganese superoxide dismutase analog and recovering the analog so produced.

8. A method of producing an enzymatically active analog of human manganese superoxide dismutase having the superoxide dismutase activity of naturally-occurring human manganese superoxide dismutase which comprises:

growing a culture of *Escherichia coli* cells in a production medium supplemented with a non-growth inhibitory amount of $Mn^{++}$ such that the concentration of $Mn^{++}$ in the medium while the cells are growing is greater than 2 ppm, wherein said cells contain a plasmid which contains DNA comprising nucleotides 115-708 of FIG. 1 encoding the analog of human manganese superoxide dismutase and the cells are capable of expressing the DNA encoding the analog of human manganese superoxide dismutase and wherein said culture is grown under suitable conditions such that the DNA is expressed and the analog of human manganese superoxide dismutase is produced in the bacterial cells at an expression level of about 5-25% of total bacterial protein; and recovering the enzymatically active analog of human manganese superoxide dismutase so produced.

9. A method of claim 8, wherein the plasmid is designated pMSE-4 and is deposited in *Escherichia coli* strain A4255 under ATCC Accession No. 53250.

10. A method of claim 8, wherein the plasmid is designated pMS≠RB4.

11. A method of claim 8, wherein the production medium is a casein hydrolysate medium.

12. A method of claim 8, wherein the production medium is LB medium.

13. A method of claim 8, wherein the MN++ concentration is from about 50 to about 1500 ppm.

14. A method of claim 13, wherein the Mn++ concentration is about 150 ppm.

15. A method of claim 13, wherein the Mn++ concentration is about 750 ppm.

16. A method of claim 8, wherein the *Escherichia coli* cells are *Escherichia coli* strain A4255 containing a plasmid designated pMSE-4 and deposited under ATCC Accession No. 53250.

17. A method of claim 8, wherein the *Escherichia coli* cells are *Escherichia coli* strain A4255 containing the plasmid designated pMSΔRB4.

18. A method according to claim 8 wherein the expression level is about 10-20% of total bacterial protein.

19. A plasmid designated pMSG11-1 and deposited in *Escherichia coli* strain MC1061 under ATCC Accession No. 67363.

20. A plasmid designated pMSG4 and deposited in *Escherichia coli* strain MC1061 under ATCC Accession No. 67364.

21. A plasmid designated pMSG-1b and deposited in *Escherichia coli* strain MC1061 under ATCC Accession No. 67365.

* * * * *

UNITED STATES PATENT AND TRADEMARK OFFICE
CERTIFICATE OF CORRECTION

PATENT NO. : 5,270,195          Page 1 of 2
DATED      : December 14, 1993
INVENTOR(S): Jacob R. Hartman and Yaffa Beck It is certified that error appears in the above-indentified patent and that said Letters Patent is hereby corrected as shown below:

Title page, Item: [63] in Related U.S. Application Data, "Ser. No. 32,734, Sep. 27, 1987, abandoned" should read --Ser. No. 32,734, Mar. 27, 1987, abandoned--;

Drawing Sheet 12 of 14 should be labelled --Figure 7;--;

Column 1, line 27, "$(O_2-)$" should read --$(O_2^-)$--;

Column 1, line 35, "$2O_2- + {}_2H^+$" should read --$2O_2^- + 2H^+$--;

Column 3, line 1, "(NA" should read --DNA--;

Column 3, line 56, "pMS RB4" should read --pMSΔRB4--;

Column 4, line 4, "$2O_2-$" should read --$2O_2^-$--;

Column 5, line 26, "in 6" should read --in FIG. 6--;

Column 10, line 24, "$2O_{2\_}$" should read --$2O_2^-$--;

Column 12, line 35, "(KOAC)" should read --(KOAc)--;

Column 13, line 31, "or" should read --of--;

UNITED STATES PATENT AND TRADEMARK OFFICE
CERTIFICATE OF CORRECTION

PATENT NO. : 5,270,195
DATED : December 14, 1993
INVENTOR(S) : Jacob R. Hartman and Yaffa Beck It is certified that error appears in the above-indentified patent and that said Letters Patent is hereby corrected as shown below:

Column 13, line 33, "PyuII" both occurrences should read --PvuII--;

Column 17, line 42, "A600" should read --OD 600--;

Column 18, line 48, "spl ice" should read --splice--;

Column 22, line 16, "27. Journal" should read --27. EMBO Journal--;

Claim 10, column 23, line 14, "pMS≠Rb4" should read --pMSΔRB4--;

Claim 13, column 23, line 29, "MN⁺⁺" should read --$Mn^{++}$--.

Signed and Sealed this

Fifth Day of March, 1996

Attest:

BRUCE LEHMAN

*Attesting Officer*   *Commissioner of Patents and Trademarks*